United States Patent [19]

Fuchs et al.

[11] Patent Number: 5,894,074
[45] Date of Patent: Apr. 13, 1999

[54] PREPARATION OF TERTIARY AMINES FROM NITRILES AND SECONDARY AMINES

[75] Inventors: Eberhard Fuchs, Frankenthal; Boris Breitscheidel, Limburgerhof; Rainer Becker, Bad Dürkheim; Horst Neuhauser, Dudenhofen, all of Germany

[73] Assignee: BASF Aktiengesellschaft, Ludwigshafen, Germany

[21] Appl. No.: 09/050,918

[22] Filed: Mar. 31, 1998

[30] Foreign Application Priority Data

Apr. 1, 1997 [DE] Germany .............. 197 13 383

[51] Int. Cl.$^6$ .................................. C07C 209/48
[52] U.S. Cl. ................ 564/490; 564/491; 564/492
[58] Field of Search ................. 564/490, 491, 564/492

[56] References Cited

U.S. PATENT DOCUMENTS 5,463,130 10/1995 Witzel et al. .
5,557,011  9/1996 Witzel et al. .

FOREIGN PATENT DOCUMENTS 424 764   5/1991  European Pat. Off. .
42 39 782  6/1994  Germany .
44 07 466  9/1995  Germany .

OTHER PUBLICATIONS

Hydrogenation of Nitriles, Chapter 4, Volf et al., Prague Inst. Of Chem. Tech., Suchbatarova 1905, 166 28 Prague 6—Dejvice, pp. 105–144.

Studien uber den Mechanismus, von Karl Kindler, pp. 113–127, 1970.

*Primary Examiner*—Brian Burn
*Attorney, Agent, or Firm*—Keil & Weinkauf

[57] ABSTRACT

A process for preparing amines of the general formula (I)

$$X(-CH_2-NR^1R^2)_n \quad (I)$$

where $R^1$ and $R^2$ are preferably methyl, X is preferably 1,4-butylene and n is preferably 2, comprises reacting nitriles of the general formula (II)

$$(R^1R^2N-CH_2-)_{n-m}X(-CN)_m \quad (II)$$

where $R^1$, $R^2$ and X are each as defined above and m is an integer from 1 to n, with secondary amines of the general formula (III)

$$HNR^1R^2 \quad (III)$$

where $R^1$ and $R^2$ are each as defined above, and hydrogen at from 50 to 250° C. and from 5 to 350 bar in the presence of a palladium catalyst comprising, based on the total weight of the catalyst, from 0.1 to 10% by weight of Pd and from 0.01 to 10% by weight of at least one further metal selected from groups IB and VII of the Periodic Table, cerium and lanthanum on a support.

10 Claims, No Drawings

PREPARATION OF TERTIARY AMINES FROM NITRILES AND SECONDARY AMINES

This invention relates to a process for preparing tertiary amines from nitriles and secondary amines over a palladium catalyst.

Processes for preparing tertiary amines from nitriles and secondary amines over certain palladium catalysts are known.

DE-A-4 239 782 describes a process for preparing diamines by reacting dinitriles with secondary amines. Specifically, adiponitrile is reacted with dimethylamine and hydrogen in the presence of a palladium catalyst to form tetramethylhexamethylenediamine. Catalysts used are 4% of Pd on $Al_2O_3$, 0.5% of Pd on $Al_2O_3$ with 20% of CaO, 1% of Pd on $Al_2O_3$ with 20% of MgO and 0.5% of Pd, 5% of Pr on $Al_2O_3$.

DE-A-4 407 466 describes a process for preparing peralkylated amines. The peralkylated amines are obtained by reacting nitriles with secondary amines and hydrogen in the presence of palladium catalysts. Specifically, 3-dimethylaminopropionitrile and dimethylamine are reacted to form tetramethylpropylenediamine, 3-hydroxypropionitrile and dimethylamine are reacted to form 3-dimethylaminopropanol and piperazine is reacted with acetonitrile to form N-ethylpiperazine. Catalysts used are 0.5% by weight of Pd on $Al_2O_3$ with 20% by weight of CaO, 0.5% by weight Pd and 5% by weight of Pr on $Al_2O_3$ or 0.5% by weight of Pd on $Al_2O_3$.

Existing catalysts are in need of improvement for some applications with regard to selectivity, conversion and onstream time.

Cerveny, Studies in surface science and catalysis 27 (1986), 105 to 144, states in connection with the preparation of tertiary amines from nitrites in the presence of a platinum catalyst that the conversion is generally incomplete owing to the strong adsorption of the tertiary amines on the catalyst surface.

It is an object of the present invention to provide a process for preparing tertiary amines by reaction of nitriles with secondary amines and hydrogen in the presence of a palladium catalyst having a superior onstream time compared with existing processes.

We have found that this object is achieved by a process for preparing amines of the general formula (I)

$$X(-CH_2-NR^1R^2)_n \quad (I)$$

where $R^1$ and $R^2$ are singly $C_{1-200}$-alkyl, $C_{3-8}$-cycloalkyl, $C_{4-20}$-alkylcycloalkyl, $C_{4-20}$-cycloalkylalkyl, $C_{2-20}$-alkoxyalkyl, aryl, $C_{7-20}$-alkylaryl, $C_{7-20}$-aralkyl, $C_{2-8}$-hydroxyalkyl, $C_{2-8}$-mercaptoalkyl, $C_{8-20}$aryloxyalkyl or together an unsubstituted or $C_{1-4}$-alkyl-monosubstituted, -disubstituted or -trisubstituted, saturated or unsaturated $C_{2-6}$-alkylene chain with or without interruption by oxygen, X is unsubstituted or $C_{1-20}$-alkyl-, $C_{3-8}$-cycloalkyl-, $C_{4-20}$-alkylcycloalkyl-, $C_{4-20}$-cycloalkylalkyl-, $C_{2-20}$-alkoxyalkyl-, aryl-, $C_{7-20}$-alkylaryl-, $C_{7-20}$-aralkyl-, $C_{1-20}$-alkoxy-, hydroxy-, $C_{1-20}$-hydroxyalkyl-, amino-, $C_{1-20}$-alkylamino-, $C_{2-20}$-dialkylamino-, $C_{2-12}$-alkenylamino-, $C_{3-8}$-cycloalkylamino-, arylamino-, diarylamino-, aryl-$C_{1-8}$-alkylamino-, halogen-, mercapto-, $C_{2-20}$-alkenyloxy-, $C_{3-8}$-cycloalkoxy-, aryloxy-, $C_{2-8}$alkoxycarbonyl-substituted $C_{1-20}$-alkyl, $C_{2-20}$-alkenyl or $C_{3-8}$cycloalkyl having n free valences, and n is an integer from 1 to 4, which comprises reacting nitriles of the general formula (II)

$$(R^1R^2N-CH_2-)_{n-m}X(-CN)_m \quad (II)$$

where $R^1$, $R^2$ and X are each as defined above and m is an integer from 1 to n, with secondary amines of the general formula (III)

$$HNR^1R^2 \quad (III)$$

where $R^1$ and $R^2$ are each as defined above, and hydrogen at from 50 to 250° C. and from 5 to 350 bar in the presence of a palladium catalyst comprising, based on the total weight of the catalyst, from 0.1 to 10% by weight of Pd and from 0.01 to 10% by weight of at least one further metal selected from groups IB and VIII of the Periodic Table, cerium and lanthanum on a support.

This invention is based on the finding that use of an above-defined catalyst for reacting secondary amines with nitrites and hydrogen to form tertiary amines Leads to better catalyst onstream time or long-term stability.

Contrary to the Cerveny reference cited at the beginning, which recites the disadvantages of using platinum catalysts for converting nitriles into tertiary amines, it was found that the combination of palladium with at least one further metal selected from the groups IB and VIII of the Periodic Table of the Elements, cerium and lanthanum, especially platinum or lanthanum, provides improved catalysts for the above process.

The catalysts used according to the present invention comprise, based on the total weight of the catalyst, from 0.1 to 10% by weight, preferably from 0.3 to 5% by weight, particularly preferably from 0.5 to 1% by weight, of palladium.

They further comprise, based on the total weight of the catalyst, from 0.01 to 10% by weight, preferably from 0.01 to 5% by weight, particularly preferably from 0.05 to 2% by weight, especially from 0.05 to 0.2% by weight, of at least one further metal selected from groups IB and VII of the Periodic Table of the Elements, cerium and lanthanum. It is possible to use one further metal or a mixture of more than one further metals. Preference is given to copper, platinum and mixtures thereof, particular preference being given to platinum. Particular preference is given to a catalyst comprising from 0.3 to 5% by weight of palladium and from 0.01 to 5% by weight of platinum, especially from 0.5 to 1% by weight of palladium and from 0.05 to 0.2% by weight of platinum, based on the total weight of the catalyst. Particular preference is likewise given to a catalyst comprising from 0.3 to 5% by weight of palladium and from 0.01 to 5% by weight of lanthanum, especially from 0.5 to 1% by weight of palladium and from 1 to 5% by weight of lanthanum, based on the total weight of the catalyst.

Particular preference is given to a catalyst comprising about 0.9% by weight of Pd and about 0.1 % by weight of Pt, based on the total weight of the catalyst, on $ZrO_2$ as support and to a catalyst comprising about 0.9% by weight of Pd and about 3% by weight of lanthanum, based on the total weight of the catalyst, on $Al_2O_3$ or $SiO_2$ as support.

The support can be any known suitable support. For example, the support is selected from activated carbon, silicon carbide and metal oxides. The metal oxides used are preferably aluminum oxide, silicon dioxide, titanium dioxide, zirconium dioxide, zinc oxide, magnesium oxide or mixtures thereof, which are optionally doped with alkali and/or alkaline earth metal oxides. Particular preference is given to using -y-aluminum oxide, silicon dioxide, zirconium dioxide or titanium oxide or mixtures thereof. The supports can be used in any desired form, for example as extrudates (in the form of strands), pellets or tablets. The catalysts can be prepared according to commonly known processes, for example by impregnating the support with solutions of compounds of the metals used. Palladium, for example, can be applied by impregnating the support with solutions of $PdCl_2$ or $Pd(NO_3)_2$.

The supports can be coated, for example, with metal precursors. Suitable metal precursors are metal salts, such as nitrates, nitrosylnitrates, halides, carbonates, carboxylates, acetylacetonates, chloro complexes, nitrito complexes and amine complexes. Preference is given to nitrates, chlorides, chloro complexes and amine complexes. Application is preferably by impregnating. The metal precursors to the metals can be applied simultaneously or in succession. The order in which the active components are applied is freely electable.

Further methods for preparing the catalysts used according to the present invention are known to one of ordinary skill in the art and include vapor deposition, sputtering and coprecipitation.

The surface area, pore volume and the pore size distribution of the catalyst are uncritical over wide ranges.

The process of the present invention is carried out at from 50 to 200° C., preferably at from 90 to 170° C., particularly preferably at from 120 to 160° C., and at from 5 to 300 bar, preferably at from 50 to 250 bar, particularly preferably at from 70 to 210 bar, batchwise or preferably continuously in pressure apparatus such as autoclaves or preferably in a tubular reactor. The pressure employed is preferably the hydrogen pressure in the reactor. If a tubular reactor is used, the catalyst used can also be present as a fixed-bed catalyst.

The reactor is charged with the nitrile of the general formula (II) and the secondary amine of the general formula (III) in the molar ratio based on one nitrile group which is preferably within the range from 1:1 to 30:1, especially within the range from 1:1 to 15:1, particularly preferably within the range from 1.1:1 to 5:1. However, larger amine excesses or else amine deficiencies can also be employed.

The process of the present invention can be carried out without a solvent or in solvents such as water, methanol, ethanol, tetrahydrofuran, methyl tert-butyl ether or N-methylpyrrolidone. The solvent used can be a solvent for the nitrile of the general formula (II) and/or for the secondary amine of the general formula (III) and/or for the ammonia formed in the course of the reaction. The process of the present invention is preferably carried out without a solvent.

The amines of the general formula (I) obtained in the process of the present invention can be separated from the reaction mixture and purified in a conventional manner, for example by distillation.

The process of the present invention converts nitriles of the general formula (II)

(II)

where

X is unsubstitted or $C_{1-20}$-alkyl-, $C_{3-8}$-cycloalkyl-, $C_{4-20}$-alkylcycloalkyl-, $C_{4-20}$-cycloalkylalkyl-, $C_{2-20}$-alkoxyalkyl-, aryl-, $C_{7-20}$-alkylaryl-, $C_{7-20}$-aralkyl-, $C_{1-20}$-alkoxy-, hydroxy-, $C_{1-20}$-hydroxyalkyl-, amino-, $C_{1-20}$-alkylamino-, $C_{2-20}$-dialkylamino-, $C_{2-12}$-alkenylamino-, $C_{3-8}$-cycloalkylamino-, arylamino, diarylamino-, aryl-$C_{1-8}$-alkylamino-, halogen-, mercapto-, $C_{2-20}$-alkenyloxy-, $C_{3-8}$-cycloalkoxy-, aryloxy-, $C_{2-8}$-alkoxycarbonyl-substituted $C_{1-20}$-alkyl, $C_{2-20}$-alkenyl or $C_{3-8}$-cycloalkyl having n free valences, and n is an integer from 1 to 4.

X is preferably $C_{1-12}$-, particularly preferably $C_{1-8}$-, especially $C_{1-6}$-, specifically $C_{1-4}$-alkyl, which can be branched or unbranched and is preferably unbranched. Examples are unbranched radicals composed of 1, 2, 3, 4, 5, 6, 7, 8, 9, 10, 11, 12, 13, 14, 15, 16, 17, 18, 19, 20 methylene units, C(C)—C—C, C—C(C)—C, C—C(C)$_2$—C as structural units. Preferred structural units are C, C—C, C—C—C, C—C—C—C, C—C—C—C—C, C—C(C)—C—C, C—C(C)—C—C, C—C—C(CN)—C—C—C, particularly preferably C, C—C, C—C—C, C—C—C—C.

X can be substituted as indicated above. The number of substituents can be equal to the number of substitutable hydrogen atoms in X. Depending on the type of radical, from 1 to 5, preferably from 1 to 3, especially 0, 1 or 2, substituents can be present. Suitable substituents are:

$C_{1-20}$-alkoxy, preferably $C_{1-8}$-alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, particularly preferably $C_{1-4}$-alkoxy such as methoxy, ethoxy, n-propoxy, isopropoxy, n-butoxy, isobutoxy, sec-butoxy and tert-butoxy, hydroxyl, $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 2-hydroxy-2-propyl and 3-hydroxy-n-propyl, amino, $C_{1-20}$-alkylamino, preferably $C_{1-8}$-alkylamino, particularly preferably $C_{1-4}$-alkylamino such as methylamino, or corresponding aminoalkyl, 1-aminoethyl, 2-aminoethyl, 2-amino-n-propyl and 3-amino-n-propyl, $C_{2-20}$-dialkylamino, preferably $C_{2-12}$-dialkylamino, in particular $C_{2-8}$dialkylamino such as N,N-dimethylamino, N,N-diethylamino, N,N-dipropylamino, N,N-di-(1-methylethyl)amino, N,N-dibutylamino, N,N-di(1-methylpropyl)amino, N,N-di (2-methylpropyl)amino, N,N-di(1,1-dimethylethyl) amino, N-ethyl-N-methylamino, N-methyl-N-propylamino, N-methyl-N-(1-methylethyl)amino, N-butyl-N-methylamino, N-methyl-N-(1,1-methylpropyl)amino, N-methyl-N-(2methylpropyl) amino, N-(1,1-dimethylethyl)-N-methylamino, N-ethyl-N-propylamino, N-ethyl-N-(1,1-methylethyl) amino, N-butyl-N-ethylamino, N-ethyl-N-(1,1-methylpropyl)amino, N-ethyl-N-(2-methylpropyl) amino N-ethyl-N-(1,1-dimethylethyl)amino, N-(1,1-methylethyl)-N-propylamino, N-butyl-N-propylamino, N-(1,-methylpropyl)-N-propylamino, N-(1-methylpropyl)-N-propylamino, N-(2-methylpropyl)-N-propylamino, N(1,1-dimethylethyl)-N-propylamino, N-butyl-N-(1-methylethyl)amino, N-(1-methylethyl)-N-(1-methylpropyl)amino, N-(1-methylethyl)-N-(1-methylpropyl)amino, N-(1-methylethyl)-N-(2-methylpropyl)amino, N-(1,1-dimethylethyl)-N-(1- methylethyl)amino, N-butyl-N-(1-methylpropyl) amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, $C_{3-12}$-azacycloalkyl, preferably $C_{3-8}$-azacycloalkylamino, particularly preferably $C_{5-8}$-azacycloalkyl such as pyrrolidine, piperidine, azepan, piperazine, N-alkylpiperazine and morpholine, $C_{3-8}$-cycloalkylamino such as cyclopropylamino, cyclobutylamino, cyclopentylamino, cyclohexylamino, cycloheptylam ino and cyclooctylamino, preferably cyclopentylamino, cyclohexylamino and cyclooctylamino, particularly preferably cyclopentylamino and cyclohexylamino.

$C_{3-8}$-dicycloalkylamino, arylamino such as phenylamino, 1-naphthylamino and 2-naphthylamino, preferably phenylamino, aryl-$C_{1-8}$-alkylamino, preferably phenyl-$C_{1-8}$-alkylamino, particularly preferably phenyl-$C_{1-4}$-alkylamino such as phenylmethylamino and phenylethylamino, halogen, preferably fluorine, chlorine and bromine, particularly preferably fluorine and chlorine, mercapto, $C_{2-20}$-oxacycloalkyl, preferably $C_{2-8}$-oxacycloalkyl, particularly preferably $C_{2-8}$-oxacycloalkyl, such as 2-tetrahydrofuranyl, 3tetrahydrofuranyl, 2-furanyl and 3-furanyl, $C_{3-8}$-cycloalkoxy such as cyclopropoxy, cyclobutoxy, cyclopentoxy, cyclohexoxy, cycloheptoxy and cyclooctoxy, preferably cyclopentoxy, cyclohexoxy, particularly preferably cyclopentoxy and cyclohexoxy, aryloxy such as phenoxy, 1-naphthoxy and 2-naphthoxy, preferably phenoxy.

It is preferable for there to be present 0, 1 or 2 substituents which are OH or $C_{2-12}$-, preferably $C_{2-6}$-, especially $C_{2-4}$-dialkylamino. More particularly, the substituents are dimethylamino or OH.

$R^1$ and $R^2$ are singly $C_{1-200}$-alkyl, $C_{3-8}$-cycloalkyl, $C_{4-20}$-alkylcycloalkyl, $C_{4-20}$-cycloalkylalkyl, $C_{2-20}$-alkoxyalkyl, aryl, $C_{7-20}$-alkylaryl, $C_{7-20}$-aralkyl, $C_{2-8}$-hydroxyalkyl, $C_{2-8}$-mercaptoalkyl, $C_{8-20}$-aryloxyalkyl or together an unsubstituted or $C_{1-4}$-alkyl-monosubstituted, -disubstituted or -trisubstituted, saturated or unsaturated $C_{2-6}$-alkylene chain with or without interruption by oxygen. Preference is given to the following radicals:

$C_{1-200}$-alkyl, preferably $C_{1-20}$-alkyl, particularly $C_{1-12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, n-nonyl, isononyl, n-decyl, isodecyl, n-undecyl, n-dodecyl and isododecyl, particularly preferably $C_{1-4}$-alkyl such as methyl, ethyl, n-propyl, isopropyl, n-butyl, isobutyl, sec-butyl, tert-butyl and also preferably $C_{40-200}$-alkyl such as polybutyl, polyisobutyl, polypropyl, polyisopropyl and polyethyl, particularly preferably polybutyl and polyisobutyl, propyl, isopropyl, n-butyl, isobutyl, sec-butyl and tert-butyl, $C_{3-8}$-cycloalkyl, such as cyclopropyl, cyclobutyl, cyclopentyl, cyclohexyl, cycloheptyl and cyclooctyl, preferably cyclopentyl, cyclohexyl and cyclooctyl, particularly preferably cyclopentyl and cyclohexyl, $C_{4-20}$-alkylcycloalkyl, preferably $C_{4-12}$-alkylcycloalkyl, $C_{4-20}$-cycloalkylalkyl, preferably $C_{4-12}$-cycloalkylalkyl, $C_{2-20}$-alkoxyalkyl, preferably $C_{2-8}$-alkoxyalkyl such as methoxymethyl, 2-methoxyethyl, 2-ethoxyethyl, 3-methoxypropyl and 3-ethoxypropyl, aryl such as phenyl, 1-naphthyl and 2-naphthyl, preferably phenyl, $C_{7-20}$-alkylaryl such as $C_{7-20}$-alkylphenyl, preferably C7-12alkylphenyl, $C_{7-20}$-aralkyl, preferably $C_{7-12}$-phenylalkyl such as benzyl, 1-phenethyl, 2-phenethyl, 1-phenylpropyl, 2-phenylpropyl, 3-phenylpropyl, 1-phenylbutyl, 1-phenylbutyl, 3-phenylbutyl and 4-phenylbutyl, particularly preferably benzyl, 1-phenethyl and 2-phenethyl, $C_{2-8}$-hydroxyalkyl, preferably $C_{2-4}$-hydroxyalkyl such as 1-hydroxyethyl, 2-hydroxyethyl, 2-hydroxy-n-propyl and 3-hydroxy-n-propyl, $C_{2-8}$-mercaptoalkyl, preferably $C_{2-4}$-mercaptoalkyl such as 1-mercaptoethyl, 2-mercaptoethyl, 2-mercapto-n-propyl and 3-mercapton-propyl, $C_{8-20}$-phenoxyalkyl, preferably $C_{8-12}$-phenoxyalkyl such as 2-phenoxyethyl, 2-phenoxypropyl, 3-phenoxypropyl, 2-phenoxybutyl, 3-phenoxybutyl and 4-phenoxybutyl, particularly preferably 2-phenoxyethyl, together an unsubstituted or $C_{1-4}$-alkyl-monosubstituted, -disubstituted or -trisubstituted, saturated or unsaturated $C_{2-6}$-alkylene chain with or without interruption by oxygen, such as $-CH_2-O-CH_2-CH_2-$, $-CH_2-CH_2-O-CH_2-CH_2-$, $-CH_2-CH_2-CH_2-CH_2-$, $-CH_2-CH_2-CH_2-O-CH_2-CH_2-CH_2-$, and $-CH_2-CH(CH_3)-CH(CH_3)-CH_2-$.

The most preferred radicals $R^1$ and $R^2$ are $C_{1-6}$-alkyl radicals, especially methyl and ethyl.

The n is an integer from 1 to 4, preferably from 1 to 3, especially 1 or 2.

The m is an integer from 1 to n, preferably equal to n.

The reaction takes place with secondary amines of the general formula (III)

$$HNR^1R^2 \qquad (III)$$

where $R^1$ and $R^2$ are each as defied above.

Preferred nitriles of the general formula (II) are acetonitrile, propionitrile, isopropionitrile, butyronitrile, valeronitrile, pentenonitrile, retenonitrile, 3-hydroxypropionitrile, 3-methoxypropionitrile, 3-ethoxypropionitrile, 3-propoxypropionitrile, 3-isopropoxypropionitrile, 3-cyclohexoxypropionitrile, 2-methyl-3-hydroxypropionitrile, 3-methoxy-2-methylpropionitrile, 3-ethoxy-2-methylpropionitrile, 2-methyl-3-propoxypropionitrile, 3-isopropoxy-2-methylpropionitrile, 3-cyclohexoxy-2-methylpropionitrile, 3-methyl-3-hydroxypropionitrile, 3-methoxy-3-methylpropionitrile, 3-ethoxy-3-methylpropionitrile, 3-methyl-3-propoxypropionitrile, 3-isopropoxy-3-methylpropionitrile, 3-cyclohexoxy-3-methyl-propionitrile, 3-aminopropionitrile, 3-methylaminopropionitrile, 3-dimethylaminopropionitrile, 3-ethylaminopropionitrile, 3-diethylaminopropionitrile, 3-propylaminopropionitrile, 3-dipropylaminopropionitrile, 3-isopropylaminopropionitrile, 3-diisopropylaminopropionitrile, 3-cyclohexylamiinopropionitrile, 3-dicyclohexylaminopropionitrile, N-(cyanoethyl)-N-methylaniline. With particular preference given to 3hydroxypropionitrile, 3-methoxypropionitrile, 3-dimethylaminopropionitrile, 3-diethylaminopropionitrile, 3-cyclohexylaminopropionitrile and 3-methylaminopropionitrile, especially biscyanoethyl ether, biscyanoethylamine, N-methylbiscyanoethylanine, N-ethylbiscyanoethylamine, N-n-propylbiscyanoethylamine, N-n-propylbiscyanoethylamine, polyisobutylenenitrile, N-polyisobutyleneaminopropionitrile, triscyanoethylamine, 5-aminovaleronitrile, 5-methylaminiovaleronitrile, 5-dimethylaminovaleronitrile, 6-aminocapronitrile, 6-methylaminocapronitrile, 6-dimethylaminocapronitrile, 5-amino-4-methylvaleronitrile, 5-methylamino-4-methylvaleronitrile, 5-diethylamino-4-methylvaleronitrile, 5-ethylamino-4-methylvaleronitrile, 5-diethylamino-4-methylvaleronitrile, 5-amino-2-methylvaleronitrile, 5-methylamino-2-methylvaleronitrile, 5-dimethylamino-2-valeronitrile, 5-ethylamino-2-methylvaleronitrile, 5-diethylamino-2-methylvaleronitrile, 4-cyanosuberonitrile.

Preference is given to suberonitrile, adiponitrile, methylglutaronitrile, methyleneglutaronitrile, glutaronitrile, succinonitrile, malononitrile, 1,2,6tricyanohexane. Particular preference is given to adiponitrile, 3dimethylaminopropionitrile and 3-hydroxypropionitrile.

Preferred secondary amines of the general formula (III) are:
dimethylamine, diethylamine, dipropylamine, diisopropylamine, di-n-butylamine, diisobutylamine, di-sec-butylamine, di-2-ethylhexylamine, ditridecylamine, dicyclohexylamine, ethylmethylamine, methylcyclohexylamine, ethylcyclohexylamine, piperazine, N-methylpiperazine, N-ethylpiperazine, diphenylamine, N-methylaniline, N-ethylaniline, diethanolamine, di-2-methoxyethylamine, di-2-ethoxyethylamine, methylethanolamine, ethylethanolamine, isopropylethanolamine, hydroxyethylaniline. Particular preference is given to dimethylamine, diethylamine and piperazine.

The tertiary amines I, preferably tetramethylhexamethylenediamine, tetramethylpropylenediamine, 3-dimethylaminopropanol, are curing agents for epoxy resins, catalysts for polyurethanes, intermediates for preparing quaternary ammonium compounds, plasticizers, corrosion inhibitors, textile assistants, dyes and emulsifiers. Polyfunctional tertiary amines are also used for preparing synthetic resins, ion exchangers, pharmaceuticals, crop protection and pest control agents.

The Examples which follow illustrate the invention.

EXAMPLES

Example 1

160 ml/h of adiponitrile (ADN) and 215 g/h of liquid dimethylamine (DMA) (2.2 mol of DMA/mol of ADN) are pumped in the upward direction through a tubular reactor (annular gap 12 mm; length 2000 mm) packed with 800 ml of catalyst (0.9% of Pd, 0.1% of Pt on zirconium dioxide; 4 mm extrudates). At the same time, 300 standard l/h of hydrogen are passed in at 200 bar. The reaction temperature is 120° C. After decompression to atmospheric, the excess dimethylamine and the ammonia formed are distilled off. The remaining hydrogenation effluent of 225 g/h comprises 92% of tetramethylhexamethylenediamine according to analysis by gas chromatography. The yield, determined by distillation, is 90%. The adiponitrile conversion is quantitative still after a run of 800 h.

Example 2

The tubular reactor of Example 1 is packed with 500 ml of the same catalyst, and 65 ml/h of ethylenecyanohydrin and 70 g/h of DMA (molar raito 1:1.6) are passed theretrough in the upward direction. The reactor temperature was 120° C. and the hydrogen pressure was 200 bar. After decompression to atmospheric and removal of ammonia/DMA, 89 GC area % of dimethylaminopropanol was obtained. The initial catalyst velocity of 0.13 l/lh was then increased, step by step, to 0.5 l/lh in the course of 1000 h, while the temperature was raised to 160° C., so that 90% of dimethylaminopropanol was still obtained toward the end of the run. No deactivation occurs, and the catalyst is mechanically intact when removed for inspection.

We claim:

1. A process for preparing amines of the general formula (I)

where
R$^1$ and R$^2$ are singly C$_{1-200}$-alkyl, C$_{3-8}$-cycloalkyl, C$_{4-20}$-alkylcycloalkyl, C$_{4-20}$-cycloalkylalkyl, C$_{2-20}$-alkoxyalkyl, aryl, C$_{7-20}$-alkylaryl, C$_{7-20}$-aralkyl, C$_{2-8}$-hydroxyalkyl, C$_{2-8}$-mercaptoalkyl, C$_{8-20}$-aryloxyalkyl or together an unsubstituted or C$_{1-4}$-alkyl-monosubstituted, -disubstituted or -trisubstituted, saturated or unsaturated C$_{2-6}$-alkylene chain with or without interruption by oxygen, X is unsubstituted or C$_{1-20}$-alkyl-, C$_{3-8}$-cycloalkyl-, C$_{4-20}$alkylcycloalkyl-, C$_{4-20}$-cycloalkylalkyl-, C$_{2-20}$alkoxyalkyl-, aryl-, C$_{7-20}$-alkylaryl-, C$_{7-20}$-aralkyl-, C$_{1-20}$-alkoxy-, hydroxy-, C$_{1-20}$-hydroxyalkyl-, amino-, C$_{1-20}$-alkylamino-, C$_{2-20}$-dialkylamino-, C$_{2-12}$alkenylamino-, C$_{3-8}$-cycloalkylamino-, arylamino-, diarylamino-, aryl-C$_{1-8}$-aikylamino-, halogen-, mercapto, C$_{2-20}$-alkenyloxy-, C$_{3-8}$-cycloalkoxy-, aryloxy-, C$_{2-8}$-alkoxycarbonyl- substituted C$_{1-20}$-alkyl, C$_{2-20}$-alkenyl or C$_{3-8}$-cycloalkyl having n free valences, and n is an integer from 1 to 4, which comprises reacting nitriles of the general formula (II)

where R$^1$, R$^2$ and X are each as defined above and m is an integer from 1 to n, with secondary amines of the general formula (III)

where R$^1$ and R$^2$ are each as defined above, and hydrogen at from 50 to 250° C. and from 5 to 350 bar in the presence of a palladium catalyst comprising, based on the total weight of the catalyst, from 0.1 to 20% by weight of Pd and from 0.01 to 10% by weight of at least one further metal selected from groups IB and VIII of the Periodic Table, cerium and lanthanum on a support.

2. A process as claimed in claim 1, wherein the catalyst comprises 0.3 to 5% by weight of Pd and from 0.01 to 5% by weight of Pt or from 0.01 to 5% by weight of La.

3. A process as claimed in claim 1, wherein the support is selected from activated carbon, silicon carbide and metal oxides.

4. A process as claimed in claim 3, wherein the support is selected from $ZrO_2$, $Al_2O_2$, $SiO_2$, $TiO_2$ or mixtures thereof.

5. A process as claimed in claim 1, wherein n is 1 or 2.

6. A process as claimed in claim 1, wherein m is equal to n.

7. A process as claimed in claim 1, wherein X is linear $C_{1-6}$-alkyl having up to 2 substituents on X.

8. A process as claimed in claim 7, wherein the substituents are $C_{2-12}$-dialkylamino or OH.

9. A process as claimed in claim 1, wherein $R^1$ and $R^2$ are independently $C_{1-6}$-alkyl.

10. The process of claim 1 wherein the reaction is carried out in the absence of a solvent.

* * * * *

UNITED STATES PATENT AND TRADEMARK OFFICE
CERTIFICATE OF CORRECTION

PATENT NO. : 5,894,074
DATED : April 13, 1999
INVENTOR(S) : FUCHS et al.

It is certified that error appears in the above-identified patent and that said Letters Patent is hereby corrected as shown below:

On the title page, Item [57],

In the abstract, penultimate line, "IB and VII" should be --IB and VIII--.

Col. 8, claim 1, line 39, "aryl-$C_{1-8}$-aikylamino-," should be --aryl-$C_{1-8}$alkylamino-,--.

Signed and Sealed this

Third Day of August, 1999

Attest:

Q. TODD DICKINSON

Attesting Officer *Acting Commissioner of Patents and Trademarks*